United States Patent [19]

Habermann

[11] Patent Number: 5,331,101
[45] Date of Patent: Jul. 19, 1994

[54] PROCESS FOR PREPARATION OF AMINES FROM ALCOHOLS, ALDEHYDES OR KETONES

[75] Inventor: Clarence E. Habermann, Midland, Mich.

[73] Assignee: The Dow Chemical Company, Midland, Mich.

[21] Appl. No.: 461,600

[22] Filed: Jan. 5, 1990

[51] Int. Cl.$^5$ .......................................... C07C 209/14
[52] U.S. Cl. .................................. 564/480; 564/472; 564/473
[58] Field of Search ................. 564/472, 473, 479, 480

[56] References Cited

U.S. PATENT DOCUMENTS

| | | | |
|---|---|---|---|
| 2,349,461 | 5/1944 | Pratt et al. | 564/480 |
| 2,412,209 | 12/1946 | Dickey et al. | 564/480 |
| 2,696,475 | 12/1954 | Farrow | 502/335 |
| 2,861,995 | 11/1958 | MacKenzie | 544/358 |
| 3,087,928 | 4/1963 | Godfrey | 544/178 |
| 3,347,926 | 10/1967 | Zech | 564/480 |
| 3,390,184 | 6/1968 | Moss et al. | 564/480 |
| 3,429,925 | 2/1969 | Cour | 564/473 |
| 3,520,933 | 7/1970 | Adam et al. | 564/447 |
| 3,522,309 | 7/1970 | Kirby | 564/472 |
| 3,654,370 | 4/1972 | Yeakey | 564/480 |
| 3,714,259 | 1/1973 | Lichtenwalter et al. | 564/480 |
| 3,922,303 | 11/1975 | Takehara et al. | 564/374 |
| 4,014,933 | 3/1977 | Boettger et al. | 564/447 |
| 4,036,883 | 7/1977 | Voges et al. | 564/480 |
| 4,152,353 | 5/1979 | Habermann | 564/374 |
| 4,153,581 | 5/1979 | Habermann | 502/329 |
| 4,209,424 | 6/1980 | LeGoff et al. | 502/245 |
| 4,314,084 | 2/1982 | Martinez de Pinillos et al. | 564/480 |
| 4,409,399 | 10/1983 | Swift et al. | 564/473 |
| 4,495,369 | 1/1985 | Werner et al. | 564/480 |
| 4,532,324 | 7/1985 | Renken et al. | 564/480 |
| 4,766,245 | 8/1988 | Larkin et al. | 564/474 |
| 4,772,750 | 9/1988 | Habermann | 564/472 |
| 4,806,690 | 2/1989 | Bowman | 564/473 |

FOREIGN PATENT DOCUMENTS

| | | | |
|---|---|---|---|
| 211552 | 2/1987 | European Pat. Off. | |
| 2235992 | 2/1973 | Fed. Rep. of Germany | 564/480 |
| 679712 | 9/1952 | United Kingdom | 564/472 |

Primary Examiner—Glennon H. Hollrah
Assistant Examiner—Scott C. Rand
Attorney, Agent, or Firm—Ann K. Galbraith

[57] ABSTRACT

A process for preparing amines or imines which comprises contacting an alcohol, aldehyde, or ketone with an aminating agent in the presence of a catalyst under reaction conditions sufficient to form an amine or imine, wherein the catalyst comprises a homogeneous mixture of (a) 10-90 mole percent cobalt or an insoluble salt thereof, (b) 9-89 mole percent copper or an insoluble salt thereof, and (c) 1-20 mole percent of a metal or insoluble salt of a metal selected from the group consisting of a Lanthanum series metal, thorium, uranium, scandium, titanium, and yttrium is described. A process which employs zirconium as component (c) and which is supported on a carrier material, wherein the carrier material has been neutralized with a base, is also disclosed.

17 Claims, No Drawings

PROCESS FOR PREPARATION OF AMINES FROM ALCOHOLS, ALDEHYDES OR KETONES

BACKGROUND OF THE INVENTION

This invention relates to a catalyst and process for preparing amines from alcohols, aldehydes or cautions.

It is well-known to prepare amines from alcohols, aldehydes and cautions by the reductive amination thereof using ammonia and hydrogen. These processes are typically conducted in the presence of various metallic catalysts, as described, for example, in U.S. Pat. Nos. 3,151,113; 3,347,926; 4,036,883; and 3,654,370. In these processes, the alcohol, aldehyde or ketone is contacted with ammonia and hydrogen under elevated temperatures and pressures to convert the alcohol, aldehyde or ketone group to a primary amine group.

A wide variety of alcohols can be converted to amine using this process. For example, low molecular weight alcohols such as 2-methylbuten-1-ol-4 and diethylene glycol have been converted to the primary amines using a reductive amination (ammonolysis) process. Similarly, polyether polyols have been converted to primary amine-terminated polyethers in this manner.

The last mentioned amine-terminated polyethers have been found to be useful in preparing urea-modified polyurethanes and molded polyureas. See, e.g., U.S. Pat. Nos. 4,444,910 and 4,269,945. While their use in these applications has provided polymers with various desirable properties, notably improved stiffness and high temperature properties, these amine-terminated polyethers are so reactive that it is sometimes difficult to process them even on high pressure reaction injection molding equipment. Accordingly, their use in making polyurea polymers has been very limited.

One method to reduce the reactivity of the amine-terminated polyethers is to introduce stearic hindrance by converting the primary amine group to a secondary amine group. Methods for accomplishing this include reacting the primary amine-terminated polyether with an unsaturated compound like acrylonitrile in a Michael addition reaction to form terminal $-NH(CH_2CH_2CN)$ groups, or alkylating the primary amine. However, these methods involve an additional processing step, which increases their cost of manufacture significantly. In addition, these methods provide mixtures of products.

It would be more desirable to prepare the secondary amine-terminated polyether directly from the corresponding polyol by amination with a primary amine. However, this method has not been successful to date because with the use of previously known catalysts a large number of side reactions occur. The product therefore contains large quantities of undesired primary amine groups and some tertiary amines, as well as the desired secondary amine groups and a significant amount of residual hydroxyl groups. The problem is compounded since the species with differing terminal groups cannot be separated by any practical method.

Accordingly, it would be desirable to provide a method whereby alcohols, aldehydes or cautions are converted to amines more efficiently than previous methods. In particular, it is desirable to provide an efficient process for the amination of alcohols, aldehydes or cautions with a primary amine, whereby a secondary amine is obtained in good yield with reduced amounts of undesired by-products. In addition, it is desirable to provide a novel catalyst which provides for an improved amination process.

SUMMARY OF THE INVENTION

In one aspect, this invention is a process for preparing amines or imines by contacting an alcohol, aldehyde or ketone with an aminating agent in the presence of a catalyst under conditions effective to form an amine or imine, wherein the catalyst comprises a mixture of (a) 10–90 mole percent cobalt or an insoluble salt thereof, (b) 9–89 mole percent copper or an insoluble salt thereof, and (c) 1–20 mole percent of a metal or insoluble salt of a metal selected from the group consisting of a Lanthanum series metal, thorium, uranium, scandium, titanium, and yttrium.

In a second aspect, this invention is an amination catalyst comprising a mixture of (a) 10–90 mole percent cobalt or an insoluble salt thereof, (b) 9–89 mole percent copper or an insoluble salt thereof, and (c) 1–20 mole percent of a metal or insoluble salt of a metal selected from the group consisting of a Lanthanum series metal, thorium, uranium, scandium, titanium and yttrium.

This catalyst provides for very efficient conversion of alcohols, aldehydes and cautions to primary amines in an ammonolysis reaction. Surprisingly, the catalyst of this invention also provides for an efficient, high yield amination of alcohols, aldehydes and cautions directly to secondary amines using a primary amine aminating agent. Moreover, with this catalyst, the undesired side reactions which cause primary and tertiary amine impurities are substantially reduced. Accordingly, this catalyst is particularly useful for preparing secondary amine-terminated polyethers having a large proportion of secondary amine terminal groups.

In a third aspect, this invention is a process for preparing amines or imines by contacting an alcohol, aldehyde or ketone with an aminating agent in the presence of an effective amount of a catalyst under conditions effective to form an amine or imine, wherein the catalyst comprises a mixture of (a) 10–90 mole percent cobalt or an insoluble salt thereof, (b) 9–89 mole percent copper or an insoluble salt thereof, (c) 1–20 mole percent of a metal or insoluble salt of a metal selected from the group consisting of a Lanthanum series metal, zirconium, thorium, uranium, scandium, titanium, and yttrium; supported on a carrier material, wherein the carrier material has been neutralized with a base.

This process also provides for very efficient conversion of alcohols, aldehydes and cautions to primary amines in an ammonolysis reaction. Surprisingly, this process also provides for an efficient, high yield amination of alcohols, aldehydes and cautions directly to secondary amines using a primary amine aminating agent. When zirconium is used as component (c), this catalyst advantageously provides for increased selectivity, relative to other supported zirconium catalysts in which the carrier material has not been treated with a base.

DETAILED DESCRIPTION OF THE INVENTION

The catalytic composition of the first aspect of the invention comprises a mixture of at least three components. The first component is cobalt or an insoluble salt thereof. It comprises at least about 10 mole percent, preferably at least about 20 mole percent, and more preferably at least about 25 mole percent of the three components. Further, it comprises no greater than about 90 mole percent, preferably no greater than about 70 mole percent, and more preferably no greater than about 45 mole percent of the three components. All mole percents herein are calculated on the basis of moles of metal only, and not on the basis of moles of metal salt, when an insoluble metal salt is used.

The second component of the catalytic composition is copper or an insoluble salt thereof, which comprises at least about 9 mole percent, preferably at least about 15 mole percent, and more preferably at least about 55 mole percent of the three components. Further, it comprises no greater than about 89 mole percent, preferably no greater than about 80 mole percent, and more preferably no greater than about 70 mole percent of the three components.

The third component is a metal or an insoluble salt of a metal selected from the group consisting of a Lanthanum series metal, thorium, uranium, scandium, yttrium and titanium. This component is used in a minor amount such that a homogeneous mixture of the three components is obtained. This component advantageously comprises at least about 1 mole percent, more preferably at least about 3 mole percent, and most preferably at least about 5 mole percent; and preferably no greater than about 20 mole percent, more preferably no greater than about 15 mole percent, and most preferably no greater than about 10 mole percent of the three components. Of these metals, those which have stable isotopes, form insoluble oxides and/or which are available in significant quantities, such as cerium, neodymium, samarium, gadolinium, dysprosium, erbium, ytterbium and titanium are preferred. Most preferred, on the basis of availability, cost and performance are cerium and titanium, with cerium being most preferred.

With respect to all three components, the oxides are preferred, since the oxides are relatively insoluble, and are generally easily prepared by heating and decomposing soluble salts such as nitrates. This provides for a convenient method of preparing mixtures of the three components.

In addition to the foregoing components, small quantities of other metals or insoluble salts thereof can be present in the catalytic composition. Examples of these metals include groups VIIIB metals, zinc, silver, gold, zirconium and the like. Preferably, however, such additional metals are not present. When present, however, they are preferably present in the form of their oxides, and advantageously comprise less than about 30, more preferably less than about 20 mole percent of the metals in the composition.

In a third aspect, this invention is a process for preparing amines or imines by contacting an alcohol, aldehyde or ketone with an aminating agent in the presence of an effective amount of a catalyst under conditions effective to form an imine or amine, wherein the catalyst comprises a mixture of (a) 10-90 mole percent cobalt or an insoluble salt thereof, (b) 9-89 mole percent copper or an insoluble salt thereof, (c) 1-20 mole percent of a metal or insoluble salt of a metal selected from the group consisting of a Lanthanum series metal, zirconium, thorium, uranium, scandium, titanium, and yttrium; supported on a carrier material, wherein the carrier material has been neutralized with a base.

Components (a), (b), (c) are preferably combined in amounts as described above for the catalyst of the process of the first aspect of the invention. When zirconium is used as component (c), it is preferably used in the same amounts as those specified above for a Lanthanum series metal, thorium, uranium, scandium, titanium, or yttrium.

If a supported catalyst is desired, the metal salts can be precipitated directly upon or with the carrier (support) in the preparation of the catalyst. Any support which will withstand the amination reaction conditions described herein can be used in the process of the present invention. Examples of supports include pumice, silica gel, asbestos, diatomaceous earth, fullers earth, aluminum oxide, titania, zirconia, silica-alumina, magnesia, magnesium silicate, silicon carbide, silicalite, and silica. Preferred supports include silica, aluminum oxide, and titania, with titania being the most preferred. When titania is selected as a support, the catalyst of the invention may comprise the support, cobalt, and copper, since the titania may provide sufficient titanium to suffice as component (c) of the catalyst.

According to the process of the third aspect of the invention, when a catalyst support is used, it is neutralized with a base prior to the deposition of the catalyst on the carrier material. The term "neutralized" as used herein means that most of the acid sites present on the carrier material (support) are reacted with a base. Preferably, at least about 50 percent, and more preferably at least about 90 percent of such sites are reacted with a base. This treatment typically improves the selectivity of the catalyst 20-50 percent. The support may be treated with any base which will adhere to the support and neutralize its acidic sites. Preferably, the base is an alkali metal hydroxide, and is more preferably sodium hydroxide or potassium hydroxide, or a combination thereof. While the number of acid sites present on the catalyst support will depend on the support and the calcination conditions, the support is preferably treated with a solution of base wherein the base is present in an amount, based on the weight of the support, of at least about 0.5 percent, of no greater than about 6 percent, and more preferably about 3 percent. Preferably, the support is contacted with the base for about an hour, and then dried in an oven for about an hour.

The catalytic composition of either aspect of the invention can be prepared in any convenient manner, as long as the components are intimately and homogeneously mixed. The catalyst of the invention may be prepared by contacting a solution of nitrate or chloride metal salts with a solution of ammonium carbonate under reaction conditions sufficient to form a metal hydroxy carbonate and ammonium nitrate or ammonium chloride. Nitrate metal salts are preferred because they can be easily removed by washing the catalyst and, if they remain unreacted in the reaction mixture, they will typically decompose at temperatures at which the catalyst is later calcined. Chloride metal salts tend to form insoluble oxychlorides which, if not completely removed from the reaction mixture, may inhibit catalytic activity. Sodium bicarbonate and sodium carbonate may be used instead of ammonium carbonate, although ammonium carbonate is preferred since it will easily decompose under calcination conditions.

The concentration of the metal salt solution and the ammonium carbonate solution is preferably in the range of from about 0.5M to about 5M, and the solutions are preferably contacted at a temperature in the range of from about 0° C. to about 90° C. These reaction conditions are preferred since they advantageously produce a homogeneous catalyst. The pH of the reaction mixture is preferably at least about 6, and is preferably no greater than about 7.0, and is more preferably maintained at about 6.5, so that the metal hydroxy carbonate formed in the reaction will advantageously more readily precipitate out of solution.

If titanium is selected as one of the catalytic metals, a solution of titanium alkoxide may be added to the reaction mixture to prepare a titanium catalyst. When titanium alkoxide is added to the reaction mixture, it is preferably mixed simultaneously with the ammonium carbonate and metal salts solution, so that titanium hydroxide, and the cobalt and copper hydroxy carbonates may precipitate together.

The precipitated metals are then separated from the reaction mixture, dried, and calcined, preferably at a temperature in the range of from about 280° C. to about 300° C., to form a mixture of metal oxides. Higher temperatures may result in a loss of surface area on the catalyst, since the oxides and metals may sinter at such temperatures, especially when working with small particle sizes. The metal oxides are then preferably pelletized, so that they may be easily used in a fixed or packed bed.

A catalytic amount of the catalyst described above is required for the process of the invention. The minimum amount of catalyst required will vary with the process reagents and reaction conditions, but the amount of catalyst employed is preferably at least about 0.1 weight percent, more preferably at least about 1 weight percent, and preferably no greater than about 5 weight percent, based on the weight of the starting materials.

Any alcohol that can be used in known ammonolytic methods can be used in the practice of this invention. These alcohols comprise a wide variety of hydroxy-containing materials. Representative alcohols include: primary and secondary $C_{1-18}$ alkanols, such as methanol, n-propanol, isopropanol, n-butanol, sec-butanol, isobutanol, pentanol, hexanol, 2-ethylhexanol, tridecanol, stearyl alcohol; $C_{5-12}$ cycloalkanols such as cyclohexanol and cycloheptanol; $C_{7-40}$ aralkanols such as benzyl alcohol and 2-phenyl ethanol; $C_{2-15}$ polyhydric alcohols such as ethylene glycol, propylene glycol, 1,3-butanediol, 1,4-butanediol, 1,5-pentanediol, hexamethylene glycol, decamethylene glycol, 1,12-dihydroxyoctadecane, or glycerol; polymeric polyhydric alcohols such as polyvinyl alcohol; glycol ethers and polyalkylene glycol ethers such as methyl glycol, ethyl glycol, butyl glycol, diethylene glycol, triethylene glycol, tetraethylene glycol, high molecular weight polyethylene glycols, dipropylene glycol, tripropylene glycol, polypropylene glycol ether, or polybutylene glycol ether; aminated alcohols such as alkanolamines, including ethanolamine, propanolamine, isopropanolamine, hexanolamine, diethanolamine, diisopropanolamine, or dimethylethanolamine; and aminated polyhydric alcohols and glycol ethers such as aminated polyethylene glycol. Other suitable hydroxy-containing compounds are disclosed in U.S. Pat. Nos. 3,347,926, 3,654,370, and 4,014,933, the relevant portions of which are hereby incorporated by reference.

Any aldehyde or ketone that can be used in known ammonolytic methods can be used in the practice of the process of the invention. Examples of such aldehydes include: methanal, ethanal, propanal, butanal, cyclohexanal, benzylaldehyde, and aldehydes prepared from the dehydrogenation of polyhydric alcohols, polymeric polyhydric alcohols, glycol ethers and polyalkylene glycol ethers, aminated alcohols, and aminated polyhydric alcohols and glycol ethers. Representative ketones include: propanone butanone, 2-pentanone, 3-pentanone, 3-methyl-2-butanone, 1-phenyl-2-propanone, acetophenone, n-butyrophenone, benzophenone, 3-nitro-4'-methylbenzophenone, and ketones prepared from the dehydrogenation of polyhydric alcohols, glycol ethers and polyalkylene glycol ethers, aminated alcohols, and aminated polyhydric alcohols and glycol ethers.

Aminating agents useful in the process of this invention are ammonia, primary amines, and secondary amines. The primary and secondary amines generally have $C_{1-12}$ alkyl groups, $C_{5-8}$ cycloalkyl groups, or $C_{7-40}$ aralkyl groups and include such compounds as: methylamine, dimethylamine, ethylamine, diethylamine, isopropylamine, diisopropylamine, n-butylamine, sec-butylamine, isobutylamine, ethylenediamine, benzylamine, cyclohexylamine, and aniline. Other suitable amines include cyclic amines which can contain hetero atoms other than nitrogen, such as oxygen, and include, for example, morpholine, pyrrolidine, piperidine, and piperazine. Although combinations of the above-described aminating agents may be used, the use of a single agent is preferred.

At least a stoichiometric amount of aminating agent, relative to the amount of alcohol is required for the practice of this invention. However, for reasons of convenience and efficiency it is preferably to practice this invention with a stoichiometric excess of aminating agent to alcohol. Preferably, the ratio of aminating agent:alcohol is at least about 1:1, and more preferably at least about 10:1, and is preferably no greater than about 200:1, and is more preferably no greater than about 20:1. Preferably, the aminating agent:aldehyde, ketone, or mixture mole ratios are about the same as the aminating agent:alcohol mole ratios recited above.

If metal oxides are used in the catalyst of the process of the invention, they are reduced prior to the amination process. Hydrogen is the most preferred reducing agent. Preferably, the catalyst is reduced slowly, in order to maintain good activity and surface area, before the amination process begins. For example, the catalyst may be heated to 150° C. and contacted with a 5 percent hydrogen in nitrogen feed, and then further reduced upon a gradual increase in temperature and hydrogen concentration, up to 200° C. and a 50 percent hydrogen in nitrogen feed.

The amination process of the invention is preferably carried out in the presence of hydrogen, since hydrogen will advantageously keep the catalyst clean and prevent discoloration of the product. During the amination process, the amount of hydrogen employed is preferably an amount sufficient such that the hydrogen:alcohol mole ratio is at least about 0.1:1, more preferably is at least about 1:1, and most preferably at least about 2:1. Preferably, the hydrogen:alcohol mole ratio is no greater than about 100:1, more preferably no greater than about 50:1, and most preferably no greater than about 40:1. The preferred hydrogen:aldehyde, ketone, or mixture mole ratios are the same as the hydrogen:alcohol mole ratios recited above. For example, typical feed flow rates of the mixture of the aminating agent and alcohol, ketone, aldehyde, or mixture thereof might vary from 5 cc/hour to 500 cc/hour per liter of catalyst, with the hydrogen flow ranging from 10 cc/min to 1000 cc/min per liter of catalyst, with both flow rates depending on the size of the catalyst bed.

The process of the invention may be conducted at any temperature which will allow the reaction to proceed, but is preferably at least about 150° C., more preferably at least about 175° C., and most preferably at least about 200° C., and is preferably no greater than about 275° C., more preferably no greater than about 240° C., and most preferably no greater than about 225° C. The process of the invention is preferably conducted at a pressure of at least about 15 psia, more preferably at least about 500 psia, and most preferably at least about 1000 psia, and is preferably no greater than about 3000 psia, more preferably no greater than about 2000 psia, and most preferably no greater than about 1500 psia.

The process of the invention may produce a mixture of primary and secondary amines, or amines of varying molecular weight, which may be affected by the reaction conditions and alcohol/amine feed ratios. Accordingly the ratio of primary/secondary amines and the molecular weight of the products obtained may be partially controlled by the selection of such reaction conditions and feed ratios. In general, the higher the amination temperature, the higher the molecular weight of the amine product; the higher the amination reaction pressure or feed material flow rate, the higher the ratio of secondary amine; and the higher the amine/alcohol feed ratio, the higher the ratio of secondary amine. For the production of secondary amines, the process of the invention is preferably conducted at a temperature of at least about 175° C., more preferably at least about 200° C., and most preferably at least about 225° C., and preferably no greater than about 300° C., more preferably no greater than about 265° C., and most preferably no greater than about 250° C.

The process of the invention may be practiced in either a batch or continuous operation, in either a liquid or gas phase, and either neat or in the presence of an inert solvent. "Inert solvent" as used herein means that the solvent is essentially nonreactive with the process reagents and products under process reaction conditions. Examples of such inert solvents include aliphatic and aromatic hydrocarbons such as hexane, heptane, cyclohexane, benzene, toluene, and xylene; nonreactive tertiary amines such as pyridine, picoline, and lutadine. The process of the invention may also be conducted in the presence or absence of water. Preferably, water is present in amounts no greater than about 50 weight percent of the alcohol, aldehyde, ketone, or mixture thereof.

The selectivity of the process of the invention for the production of secondary amines, relative to the production of primary, secondary, and tertiary amines, is preferably at least about 95 percent, more preferably at least about 98 percent, and most preferably at least about 99 percent.

The process of the invention may be used for the amination of polyether polyols. Such aminated polyether polyols are useful in the production of urethane polymers in reaction injection molding processes, which are described, for example, in U.S. Pat. Nos. 4,444,910 and 4,296,945, the relevant portions of which are hereby incorporated by reference. Such polyols preferably have a functionality in the range of from about 2 to about 4, and a molecular weight in the range of from about 230 to about 6000.

ILLUSTRATIVE EMBODIMENTS

The following examples are given to illustrate the invention and should not be interpreted as limiting it in any way. Unless stated otherwise, all parts and percentages are given by weight. A summary of the results of these examples is shown in Table I.

EXAMPLE 1

A catalyst is prepared with the nominal composition of 25 mole percent Co, 70 mole percent Cu, and 5 mole percent Ce as follows: a solution is prepared of 73 g of $Co(NO_3)_3 6H_2O$, 168.9 g of $Cu(NO_3)_2 3H_2O$, and 16.3 g of $Ce(NO_3)_3 6H_2O$ in 4 liters of $H_2O$. A second solution is prepared of 226 g of $(NH_4)_2CO_3$ in 4720 cc of $H_2O$. The two solutions are added to a stirred flask at a constant pH of 6.5. The precipitate is stirred for an additional hour after the solutions are added and allowed to settle overnight. The precipitate is then filtered and washed until $NH_4NO_3$ is completely removed. The carbonate precipitate is dried at 70° C. for 24 hours and calcined in a muffle furnace at 290° C. for 2 hours to obtain the mixed oxide catalyst. The oxide is then pelletized to give a particle size suitable for a fixed bed catalytic reactor, or used as is in a slurry bed reactor. The catalyst is reduced prior to use, starting with 5 volume percent $H_2/N_2$ at 150° C. for 4 hours. At 4-hour intervals, the $H_2$ concentration is doubled and the temperature increased 10° C. until a 50 volume percent $H_2/N_2$ and 200° C. is attained. The reduced catalyst (6 g) is put into a stirred reactor, along with 100 g of polypropylene ether glycol (P-2000) under a nitrogen purge. Anhydrous $NH_3$ (35 g) and 400 psi $H_2$ are added and the reactor is heated for 6 hours at 210° C. with stirring. The product is filtered and volatiles are removed in a rotary vacuum flask run at 125° C. $^{13}C$ NMR and HCl titration shows a polyol conversion of 90 percent with only primary amine end groups present.

EXAMPLE 2

Using a similar catalyst preparation to that used in Example 1, except that titanium alkoxide is added as a third solution to the mixture of ammonium carbonate and the nitrate salt solution, a catalyst of nominal composition 25 mole percent Co, 70 mole percent Cu, and 5 mole percent Ti is prepared. Also using the procedure of Example 1 for the amination reaction, a 97 percent polyol conversion is obtained with only primary amine end groups being produced.

EXAMPLE 3

Using a similar catalyst preparation to that used in Example 1, a catalyst of nominal composition 25 mole percent Co, 70 mole percent Cu, and 5 mole percent Sm is prepared. Also using the procedure of Example 1 for the amination reaction, an 88 percent polyol conversion is obtained with only primary amine end groups being produced.

COMPARATIVE EXAMPLE 1

Using a similar catalyst preparation to that used in Example 1, a catalyst of nominal composition 25 mole percent Co, 70 mole percent Cu, and 5 mole percent Zr is prepared. Also using the procedure of Example 1 for the amination reaction, a polyol conversion of only 61 percent is obtained.

EXAMPLE 4

A portion of the catalyst prepared in Example 1 is used in a batch amination (slurry bed) using a stirred pressure vessel. Polypropylene ether glycol (100 g) of M.W. 2000 and 35 g of isopropylamine are weighed into the pressure vessel along with 6 g of catalyst powder, under a nitrogen purge. The catalyst had been previously reduced as described in Example 1. The reactor is pressurized to 400 psi with $H_2$, and the reaction is carried out at 225° C. for 6 hours. The reactor is stirred at 1600 rpm during the reaction period. The product is filtered and volatiles are removed in a rotating vacuum flask at 125° C. $^{13}$C NMR analyses indicate an 89 percent conversion of the alcohol end groups with only isopropylamine end groups resulting. There is no change in the molecular weight of the product as shown by Size Exclusion Chromatography (SEC). No primary amine end groups are present.

EXAMPLE 5

The same reaction conditions are run as in Example 4 using a reduced catalyst powder with a nominal composition of 25 mole percent Co, 70 mole percent Cu, and 5 mole percent Ti prepared by the procedure of Example 1, except that titanium alkoxide is added as a third solution to the mixture of ammonium carbonate and the nitrate salt solution. The result of the amination reaction is a 97 percent conversion of the polyol to amines. The amine composition is 2 percent primary amine end groups and 98 percent isopropylamine end groups. There is no change in the molecular weight of the product.

EXAMPLE 6

The same reaction conditions are run as in Example 4 using a reduced catalyst with a nominal composition of 50 mole percent Co, 45 mole percent Cu, and 5 percent Zr, prepared by impregnating an $Al_2O_3$ support. The $Na_2O$ content of the carrier is first increased to 2.27 percent by treating 100 g of $Al_2O_3$ with 0.47 g of NaOH in 37 cc of deionized water followed by drying at 300° C. in air. This treatment is intended to decrease the number of acid sites, normally present on $Al_2O_3$ carriers. This support is then impregnated with a solution containing 828 g of $Co(NO_3)_26H_2O$, 596 g of $Cu(NO_3)_22\frac{1}{2}H_2O$ and 76.1 g of $ZrO(NO_3)_22H_2O$ in 3 liters of deionized water to a 16 percent loading. A second solution consisting of 114 g of $(NH_4)_2CO_3H_2O$ in 2 liters of water is used to precipitate the metals as carbonates on the support surface. Calcination of the catalyst is carried out at 300° C. for 3 hours before they are reduced as described in Example 1. The result of the amination reaction is a 51 percent conversion of the polyol and 100 percent selectivity to isopropylamine end groups and no primary amine end groups.

EXAMPLE 7

Similar reaction conditions are used as in Example 4 using a reduced catalyst with a nominal composition of 50 mole percent Co, 45 mole percent Cu, and 5 percent Ce, prepared by the impregnation technique of Example 6. The $Al_2O_3$ support is impregnated with a solution containing 138 g of $Co(NO_3)_26H_2O$, 99.3 g of $Cu(NO_3)_23H_2O$, and 34.3 g of $Ce(NO_3)_26H_2O$ in 600 cc of deionized water for an 11 percent loading. Carbonate solution from Example 6 is used to precipitate the metal carbonates. Posttreatment of the catalyst is the same as in the previous example. The results of the amination reaction are a 94 percent polyol conversion with 100 percent selectivity to isopropylamine end groups. The molecular weight of the product has not changed from the starting material.

COMPARATIVE EXAMPLE 2

Similar reaction conditions are used as in Example 4 using a reduced zirconium catalyst with a nominal composition of 50 mole percent Co, 45 mole percent Cu, and 5 percent Zr, prepared by the impregnation technique of Example 6 without the addition of extra caustic to neutralize acid sites. The $Na_2O$ content of this support was 0.03 percent (Harshaw $Al_{14}O_4$) and the loading is 10 percent. The results of the amination reaction are a 98 percent conversion of the polyol end groups with a 56 percent selectivity to primary amine end groups and only 44 percent selectivity to isopropylamine end groups.

EXAMPLE 8

A continuous reactor system is used which is 8" long by $\frac{1}{4}$" diameter filled with 12-30 mesh catalyst particles. The catalyst with a nominal composition of 20 mole percent Co, 70 mole percent Cu, and 10 mole percent Ti is prepared as in Example 1, except that titanium alkoxide is added as a third solution to the mixture of ammonium carbonate and the nitrate salt solution, and is reduced prior to use as described in Example 1. The reactor is heated. A mixture of isopropylamine and polypropylene ether glycol (P-2000) is prepared in a molar ratio of 2:1 and pumped over the catalyst bed at 10 g/hr. Hydrogen is metered in at approximately 200 cc/minute during the run, while the temperature is maintained at 225° C. Periodic samples are collected and analyzed by $^{13}$C NMR. The results indicate a 92 percent conversion of alcohol end groups to amine end groups with all the amines present being secondary amines. Dimerization of a portion of the product results in 46 percent selectivity to 2000 MW and 54 percent to 4000 MW. No primary amine is found. The results of the foregoing examples are summarized in Table I.

TABLE I

| Example | Composition of Catalyst (mole percent) | Aminating Agent | % Conversion | % Selectivity to 1% Amine | % Selectivity to 2% Amine |
| --- | --- | --- | --- | --- | --- |
| 1 | 25% Co; 70% Cu; 5% Ce | ammonia | 90 | 100 | |
| 2 | 25% Co; 70% Cu; 5% Ti | ammonia | 97 | 100 | |
| 3 | 25% Co; 70% Cu; 5% Sm | ammonia | 88 | 100 | |
| CE 1 | 25% Co; 70% Cu; 5% Zr | ammonia | 61 | | |
| 4 | 25% Co; 70% Cu; 5% Ce | isopropylamine | 89 | | 100 |
| 5 | 25% Co; 70% Cu; 5% Ti | isopropylamine | 97 | 2 | 98 |
| 6 | 50% Co; 45% Cu; 5% Zr | isopropylamine | 51 | | 100 |
| 7 | 50% Co; 45% Cu; 5% Ce | isopropylamine | 94 | | 100 |
| CE 2 | 50% Co; 45% Cu; 5% Zr | isopropylamine | 98 | 56 | 44 |
| 8 | 20% Co; 70% Cu; 10% Ti | isopropylamine | 90 | | 100 |

What is claimed is:

1. A process for preparing secondary amines which comprises contacting an alcohol, aldehyde, or ketone with a primary amine in the presence of a catalyst under reaction conditions sufficient to form a secondary amine, wherein the catalyst comprises a homogeneous mixture of (a) 10-90 mole percent cobalt or an insoluble salt thereof, (b) 9-89 mole percent copper or an insoluble salt thereof, and (c) 1-20 mole percent of a metal or insoluble salt of a metal selected from the group consisting of a Lanthanum series metal, thorium, uranium, scandium, titanium, and yttrium.

2. The process of claim 1 wherein the catalyst comprises no greater than about 45 mole percent cobalt or an insoluble salt thereof.

3. The process of claim 1 wherein the catalyst comprises at least about 55 mole percent copper or an insoluble salt thereof.

4. The process of claim 1 wherein the catalyst comprises at least about 6 mole percent of a metal or insoluble salt of a metal selected from the group consisting of a Lanthanum series metal, thorium, uranium, scandium, titanium, and yttrium.

5. The process of claim 1 wherein component (c) is cerium or titanium.

6. The process of claim 5 wherein component (c) is titanium.

7. A process for preparing secondary amines by contacting an alcohol, aldehyde or ketone with a primary amine in the presence of an effective amount of a catalyst under conditions effective to form a secondary amine, wherein the catalyst comprises a mixture of (a) 10-90 mole percent cobalt or an insoluble salt thereof, (b) 9-89 mole percent copper or an insoluble salt thereof, (c) 1-20 mole percent of a metal or insoluble salt of a metal selected from the group consisting of a Lanthanum series metal, zirconium, thorium, uranium, scandium, titanium, and yttrium; supported on a carrier material, wherein the carrier material has been neutralized with an alkali metal hydroxide.

8. The process of claim 7 wherein the catalyst comprises no greater than about 45 mole percent cobalt or an insoluble salt thereof.

9. The process of claim 7 wherein the catalyst comprises at least about 55 mole percent copper or an insoluble salt thereof.

10. The process of claim 7 wherein the catalyst comprises at least about 6 mole percent of a metal or insoluble salt of a metal selected from the group consisting of a Lanthanum series metal, thorium, uranium, scandium, titanium, and yttrium.

11. The process of claim 7 wherein component (c) is cerium or titanium.

12. The process of claim 11 wherein component (c) is titanium.

13. The process of claim 7 wherein component (c) is zirconium.

14. The process of claim 1 wherein the alcohol, aldehyde, or ketone is a polyether polyol.

15. The process of claim 1 wherein the primary amine is isopropyl amine.

16. The process of claim 7 wherein the alcohol, aldehyde, or ketone is a polyether polyol.

17. The process of claim 7 wherein the primary amine is isopropyl amine.

* * * * *